US009017418B2

(12) United States Patent
Clausen

(10) Patent No.: US 9,017,418 B2
(45) Date of Patent: Apr. 28, 2015

(54) CONTROL SYSTEMS AND METHODS FOR PROSTHETIC OR ORTHOTIC DEVICES

(75) Inventor: Arinbjörn V. Clausen, Reykjavik (IS)

(73) Assignee: Össur hf, Reykjavik (IS)

(*) Notice: Subject to any disclaimer, the term of this patent is extended or adjusted under 35 U.S.C. 154(b) by 494 days.

(21) Appl. No.: 12/773,788

(22) Filed: May 4, 2010

(65) Prior Publication Data

US 2010/0286796 A1    Nov. 11, 2010

Related U.S. Application Data

(60) Provisional application No. 61/175,713, filed on May 5, 2009.

(51) Int. Cl.
*A61F 2/68* (2006.01)
*A61F 2/60* (2006.01)
*A61F 2/64* (2006.01)
*A61F 2/70* (2006.01)
*A61F 2/76* (2006.01)

(52) U.S. Cl.
CPC ... *A61F 2/68* (2013.01); *A61F 2/60* (2013.01); *A61F 2/605* (2013.01); *A61F 2/64* (2013.01); *A61F 2002/6827* (2013.01); *A61F 2002/704* (2013.01); *A61F 2002/7625* (2013.01); *A61F 2002/763* (2013.01); *A61F 2002/7635* (2013.01); *A61F 2002/764* (2013.01); *A61F 2002/769* (2013.01); *A61F 2250/008* (2013.01)

(58) Field of Classification Search
USPC .......................................... 623/24, 44–45, 50
See application file for complete search history.

(56) References Cited

U.S. PATENT DOCUMENTS

| 3,820,168 A | 6/1974 | Horvath |
| 3,866,246 A | 2/1975 | Seamone et al. |
| 3,995,324 A | 12/1976 | Burch |
| 4,209,860 A | 7/1980 | Graupe |
| 4,314,379 A | 2/1982 | Tanie |

(Continued)

FOREIGN PATENT DOCUMENTS

| DE | 4229330 | 3/1994 |
| EP | 1531767 | 12/2008 |

(Continued)

OTHER PUBLICATIONS

International Search Report and Written Opinion dated Sep. 1, 2010 in PCT/US2010/038886.

(Continued)

*Primary Examiner* — Bruce E Snow
(74) *Attorney, Agent, or Firm* — Knobbe Martens Olson & Bear LLP

(57) ABSTRACT

Geomagnetic methods and systems are used for monitoring the directionality of a prosthetic or orthotic device. Certain methods may include measuring multiple data points over a particular time interval to identify orientation information with respect to a prosthetic or orthotic device and/or used in the real-time control of the prosthetic or orthotic device. In certain examples, multiple points may be further compared with stored orientation data associated with predefined unsafe gait patterns. Control instructions and/or alerts based on the geomagnetic measurements can then be generated for the prosthetic or orthotic device, such as if the orientation data information matches one of the predefined unsafe gait patterns.

15 Claims, 10 Drawing Sheets

(56) References Cited

U.S. PATENT DOCUMENTS

| | | | |
|---|---|---|---|
| 4,808,187 | A | 2/1989 | Patterson et al. |
| 4,876,944 | A | 10/1989 | Wilson et al. |
| 4,878,913 | A | 11/1989 | Aebischer |
| 5,062,857 | A | 11/1991 | Berringer |
| 5,252,102 | A | 10/1993 | Singer et al. |
| 5,253,656 | A | 10/1993 | Rincoe et al. |
| 5,336,269 | A | 8/1994 | Smits |
| 5,376,128 | A | 12/1994 | Bozeman |
| 5,383,939 | A | 1/1995 | James |
| 5,413,611 | A | 5/1995 | Haslam et al. |
| 5,443,524 | A | 8/1995 | Sawamura et al. |
| 5,458,655 | A | 10/1995 | Bozeman |
| 5,480,454 | A | 1/1996 | Bozeman |
| 5,571,205 | A | 11/1996 | James |
| 5,695,527 | A | 12/1997 | Allen |
| 5,888,212 | A | 3/1999 | Petrofsky et al. |
| 5,888,213 | A | 3/1999 | Sears et al. |
| 5,893,891 | A | 4/1999 | Zahedi |
| 5,953,683 | A * | 9/1999 | Hansen et al. ........... 702/95 |
| 6,113,642 | A | 9/2000 | Petrofsky et al. |
| 6,122,960 | A | 9/2000 | Hutchings et al. |
| 6,423,098 | B1 | 7/2002 | Biedermann |
| 6,443,993 | B1 | 9/2002 | Koniuk |
| 6,517,585 | B1 | 2/2003 | Zahedi et al. |
| 6,522,266 | B1 | 2/2003 | Soehren et al. |
| 6,610,101 | B2 | 8/2003 | Herr et al. |
| 6,645,252 | B2 | 11/2003 | Asai et al. |
| 6,679,920 | B2 | 1/2004 | Biedermann et al. |
| 6,695,885 | B2 | 2/2004 | Schulman et al. |
| 6,719,806 | B1 | 4/2004 | Zahedi et al. |
| 6,740,123 | B2 | 5/2004 | Davalli et al. |
| 6,755,870 | B1 | 6/2004 | Biedermann et al. |
| 6,764,520 | B2 | 7/2004 | Deffenbaugh et al. |
| 6,875,241 | B2 | 4/2005 | Christesen |
| 7,131,998 | B2 | 11/2006 | Pasolini |
| 7,137,998 | B2 | 11/2006 | Bédard |
| 7,147,667 | B2 | 12/2006 | Bédard |
| 7,198,071 | B2 | 4/2007 | Bisbee, III et al. |
| 7,279,009 | B2 | 10/2007 | Herr et al. |
| 7,314,490 | B2 | 1/2008 | Bédard et al. |
| 7,431,737 | B2 | 10/2008 | Ragnarsdottir et al. |
| 7,455,696 | B2 | 11/2008 | Bisbee, III et al. |
| 7,531,006 | B2 | 5/2009 | Clausen et al. |
| 7,578,799 | B2 | 8/2009 | Thorsteinsson et al. |
| 7,588,604 | B2 | 9/2009 | Okuda et al. |
| 7,602,301 | B1 | 10/2009 | Stirling et al. |
| 7,637,959 | B2 | 12/2009 | Clausen et al. |
| 7,691,154 | B2 | 4/2010 | Asgeirsson et al. |
| 7,736,394 | B2 | 6/2010 | Bédard et al. |
| 7,794,505 | B2 | 9/2010 | Clausen et al. |
| 7,799,091 | B2 | 9/2010 | Herr et al. |
| 7,811,333 | B2 | 10/2010 | Jónsson et al. |
| 7,811,334 | B2 | 10/2010 | Ragnarsdottir et al. |
| 7,815,689 | B2 | 10/2010 | Bédard et al. |
| 7,862,620 | B2 | 1/2011 | Clausen et al. |
| 7,867,284 | B2 | 1/2011 | Bédard |
| 7,896,927 | B2 | 3/2011 | Clausen et al. |
| 7,953,549 | B2 | 5/2011 | Graham et al. |
| 7,955,398 | B2 | 6/2011 | Bédard et al. |
| 8,025,632 | B2 | 9/2011 | Einarsson |
| 8,048,007 | B2 | 11/2011 | Roy |
| 8,048,172 | B2 | 11/2011 | Jonsson et al. |
| 8,057,550 | B2 | 11/2011 | Clausen et al. |
| 2004/0054423 | A1 | 3/2004 | Martin |
| 2004/0064195 | A1 | 4/2004 | Herr |
| 2004/0064286 | A1 | 4/2004 | Levi et al. |
| 2005/0126026 | A1 | 6/2005 | Townsend et al. |
| 2005/0283257 | A1 | 12/2005 | Bisbee et al. |
| 2006/0135883 | A1 | 6/2006 | Jonsson et al. |
| 2006/0136072 | A1 | 6/2006 | Bisbee et al. |
| 2006/0184252 | A1 | 8/2006 | Oddsson et al. |
| 2006/0184280 | A1 | 8/2006 | Oddsson et al. |
| 2006/0249315 | A1 | 11/2006 | Herr et al. |
| 2007/0050047 | A1 | 3/2007 | Ragnarsdottlr et al. |
| 2007/0270722 | A1 | 11/2007 | Loeb et al. |
| 2009/0024062 | A1 | 1/2009 | Einarsson |
| 2009/0024065 | A1 | 1/2009 | Einarsson |
| 2009/0054996 | A1 | 2/2009 | Sykes et al. |
| 2009/0056445 | A1 | 3/2009 | Veltink |
| 2009/0171469 | A1 | 7/2009 | Thorsteinsson et al. |
| 2009/0265018 | A1 | 10/2009 | Goldfarb et al. |
| 2009/0299480 | A1 | 12/2009 | Gilbert et al. |
| 2009/0312844 | A1 | 12/2009 | Ikeuchi et al. |
| 2010/0113980 | A1 | 5/2010 | Herr et al. |
| 2010/0114329 | A1 | 5/2010 | Casler et al. |
| 2010/0185124 | A1 | 7/2010 | Bisbee et al. |
| 2010/0286796 | A1 | 11/2010 | Clausen |
| 2010/0324456 | A1 | 12/2010 | Jónsson et al. |
| 2010/0324698 | A1 | 12/2010 | Sverrisson et al. |
| 2011/0106274 | A1 | 5/2011 | Ragnarsdottir et al. |
| 2011/0125290 | A1 | 5/2011 | Langlois |
| 2011/0224804 | A1 | 9/2011 | Clausen et al. |
| 2011/0245931 | A1 | 10/2011 | Clausen et al. |
| 2011/0264230 | A1 | 10/2011 | Herr et al. |
| 2012/0016492 | A1 | 1/2012 | Clausen |

FOREIGN PATENT DOCUMENTS

| GB | 2201260 | 8/1988 |
| WO | WO 99/08621 | 2/1999 |

OTHER PUBLICATIONS

PCT International Search Report and Written Opinion, PCT/US2010/033788, dated Jul. 6, 2010.

* cited by examiner

CONTROL SYSTEMS AND METHODS FOR PROSTHETIC OR ORTHOTIC DEVICES

CROSS-REFERENCE TO RELATED APPLICATIONS

This application claims the benefit of U.S. Provisional Application No. 61/175,713, filed May 5, 2009, the entirety of which is hereby incorporated by reference.

BACKGROUND

1. Field of the Invention

Embodiments of this invention relate to controlling prosthetic or orthotic devices and, in particular, to geomagnetic sensing systems and methods for controlling such devices.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

The number of disabled persons and amputees is increasing each year as the average age of individuals increases, as does the prevalence of debilitating diseases such as diabetes. As a result, the need for prosthetic and orthotic devices is also increasing. Conventional orthoses are often used to support a joint, such as an ankle or a knee, of an individual, and movement of the orthosis is generally based solely on the energy expenditure of the user. Some conventional prostheses are equipped with basic controllers that artificially mobilize the joints without any interaction from the amputee and are capable of generating only basic motions. Such basic controllers do not take into consideration the dynamic conditions of the working environment. The passive nature of these conventional prosthetic and orthotic devices typically leads to movement instability, high energy expenditure on the part of the disabled person or amputee, gait deviations and other short- and long-term negative effects. This is especially true for leg orthoses and prostheses.

SUMMARY OF THE INVENTION

While the technology for orthotic and prosthetic devices has advanced to include basic sensor systems capable of providing some degree of feedback control, these sensors have mainly included proximity sensors, load sensors, accelerometers, tactile sensors, pressure sensors, and others. Oftentimes, these sensors are not capable of providing the prosthetic or orthotic system with the information necessary to identify a sudden change in direction and, in turn, the instructions necessary for dynamically adjusting to the changing environment. Thus, prosthetic and orthotic users can still experience instability in basic movements.

In certain embodiments of the invention, control systems and methods for motion-controlled prosthetic or orthotic devices are provided. These systems and methods include utilizing a sensor system to measure directionality and/or movement of an actively-adjustable prosthetic or orthotic system. In certain embodiments, the sensor information is then compared with defined gait patterns. If the sensor information corresponds to known unsafe gait patterns, the prosthetic or orthotic system may issue a warning and/or take other corrective action.

In one embodiment, a method for controlling an adjustable prosthetic or orthotic device is included. The method comprises measuring with a geo-magnetic sensor a plurality of data points over a time interval. The plurality of data points provides orientation data information of a prosthetic or orthotic device with respect to the earth's magnetic field. The plurality of data points are processed over the time interval by comparing the orientation data information with predefined unsafe gait patterns. Control instructions are outputted to the prosthetic or orthotic device when the orientation data information matches one of the predefined unsafe gait patterns.

In another embodiment, a motion-controlled prosthetic or orthotic device is included. The device comprises a first upper member and a second lower member moveable relative to the first upper member at a natural human joint location. The first upper and second lower members are articulated about the joint location with respect to each other. At least one geo-magnetic sensor is disposed on the motion-controlled prosthetic or orthotic device. The at least one geo-magnetic sensor is configured to monitor the directionality of the prosthetic or orthotic device with respect to the earth's magnetic field and to provide directionality data. A processor processes the directionality data and outputs a command based at least in part on the directionality data. The command comprises at least one of an alert command or an instruction to control or restrict movement of the prosthetic or orthotic device.

In another embodiment, a prosthetic or orthotic device capable of monitoring directionality and providing feedback control is included. The device comprises at least one geo-magnetic sensor disposed on an adjustable prosthetic or orthotic device. The at least one geo-magnetic sensor is configured to monitor the directionality of the device and provide directionality data. The device also comprises a processor, which processes the directionality data and outputs a command based at least in part on the directionality data. The command comprises at least one of an alert command and an instruction to control or restrict movement of the device.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to limit the invention. The following are brief descriptions of the drawings, which may not be drawn to scale.

In addition, methods and functions described herein are not limited to any particular sequence, and the blocks or states relating thereto can be performed in other sequences that are appropriate. For example, described blocks or states may be performed in an order other than that specifically disclosed, or multiple blocks or states may be combined in a single block or state.

DETAILED DESCRIPTION OF THE PREFERRED EMBODIMENTS

Figure 1A:
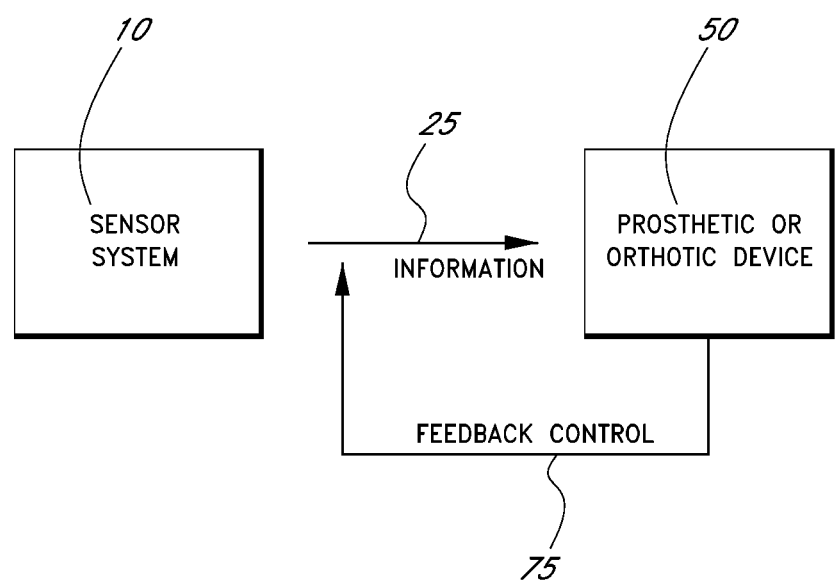
FIG. 1A illustrates a block diagram of a geo-magnetic sensing system for a prosthetic or orthotic device according to certain embodiments of the invention.

Some preferred embodiments of the invention described herein relate generally to prosthetic and orthotic systems. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The features of the systems and methods will now be described with reference to the drawings summarized above. Throughout the drawings, reference numbers are re-used to indicate correspondence between referenced elements. The drawings, associated descriptions, and specific implementation are provided to illustrate embodiments of the invention and not to limit the scope of the disclosure.

The terms "prosthetic" and "prosthesis" as used herein are broad terms and are used in their ordinary sense and refer to, without limitation, any system, device or apparatus usable as an artificial substitute or support for a body part.

The term "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

The term "ankle device" as used herein is a broad term and is used in its ordinary sense and relates to any prosthetic, orthotic or ankle-assisting device.

The term "knee device" as used herein is a broad term and is used in its ordinary sense and relates to any prosthetic, orthotic or knee-assisting device.

The term "roll" as used herein is a broad term and is used in its ordinary sense and relates to any turn or revolution about one or more real and/or imaginary axes.

The term "inclination" as used herein is a broad term and is used in its ordinary sense and relates to any angle between a reference plane and another plane or axis of direction.

The term "azimuth" as used herein is a broad term and is used in its ordinary sense and relates to any angle from a reference vector in a reference plane to a second vector in the same plane, pointing toward (but not necessarily meeting) something of interest.

Certain embodiments of the invention include a prosthetic or orthotic device coupled to a geo-magnetic sensor capable of measuring the orientation and/or movement of the device (roll, inclination, and azimuth angles) with respect to a magnetic field. Such embodiments can address disadvantageous of certain conventional prosthetic or orthotic devices that have difficulty in locating a center of gravity and/or registering absolute and relative directions and sudden changes in direction when first turned on and during use. While a typical prosthetic or orthotic device is still able to operate without this information, this may result in the user having less control and more awkward movements.

In certain embodiments, a prosthetic device that is able to measure the directional orientation and changes about an axis in the rotational orientation of the device in real time improves gait recognition and allows the user to have a quicker reaction time because the prosthetic device can quickly determine whether and how to shift its weight. Moreover, in certain embodiments, a prosthetic or orthotic device that can sense direction, such as for example, north, south, east, and west, can more quickly determine future steps and/or other movement and provide more stability in turning, for example in making a 180 degree turn or rotating around a particular point. In certain embodiments, the prosthetic device recognizes any directional change greater than 20 degrees in order to establish safer terrain sensation and response. In addition, the increase in information related to directionality can provide the extra benefit of training the user in how to make healthy movements. For example, if an orthotic user should not make certain movements (e.g., if such these movements may increase the chance of further injury), an alarm may sound to warn the user to substitute the detrimental movement with a healthier one.

Embodiments of the invention advantageously utilize geo-magnetic sensors to improve functionality and/or increase safety on prosthetic and/or orthotic devices. One example of a geo-magnetic sensor is a flux gate magnetometer. Examples of geo-magnetic sensors may include products made by Alps Electric or Yamaha Corporation. These sensors can be coupled with other types of sensors, such as for example accelerometers or gyroscopes, or with processors or controllers.

In certain embodiments, the geo-magnetic sensors are designed to measure the orientation (e.g., roll, inclination, and/or azimuth angles) of the prosthetic or orthotic device, based on movement with respect to the earth's magnetic field. For example, in certain embodiments, such measurements can be made with an accuracy of between about 0.01° and about 1.0° for the roll and inclination angles, between about 1.0° and about 2.0° for the azimuth angle, and/or with an angular resolution of about 0.1°.

In certain embodiments, the geo-magnetic sensor may be used for measuring gravitational forces as they relate to the operation of prosthetic and/or orthotic devices. In certain embodiments, the accuracy of such measurements may be between about 8.0 mg and about 9.0 mg and the resolution can be greater than about 1 mg.

In other embodiments, the geo-magnetic sensor may be used for measuring a magnetic field, such as a geomagnetic field. For example, in certain embodiments, an accuracy of such measurement may be between about 0.01 µT and about 0.2 µT with a resolution of between about 0.001 µT and about 0.01 µT. In certain embodiments, the geo-magnetic sensors operate by supplying data upon request by a processor and/or other control device associated with the prosthetic or orthotic device. In other embodiments, the geo-magnetic sensors operate by supplying data continuously.

For example, in certain embodiments, the geo-magnetic sensors may supply data in orientation format (e.g., roll, inclination, and azimuth) and/or in position format (x, y, z). In certain embodiments, the geo-magnetic sensors may range from about 0.5 mm to about 75 mm in length, width, and height and may vary in shape. In certain embodiments, the geo-magnetic sensor can operate at a temperature range of between about −10 and 50° C.

FIG. 1A illustrates a block diagram of a geo-magnetic sensing system for a motion-controlled prosthetic or orthotic device according to certain embodiments of the invention. As shown, a sensor system 10 receives input regarding the user's change in orientation/direction and sends the information 25 to a prosthetic or orthotic device 50. The prosthetic or orthotic device 50 can then process the sensory information 25 and output feedback control information 75, which may adjust the movements of the prosthetic or orthotic device 50.

Figure 1B:
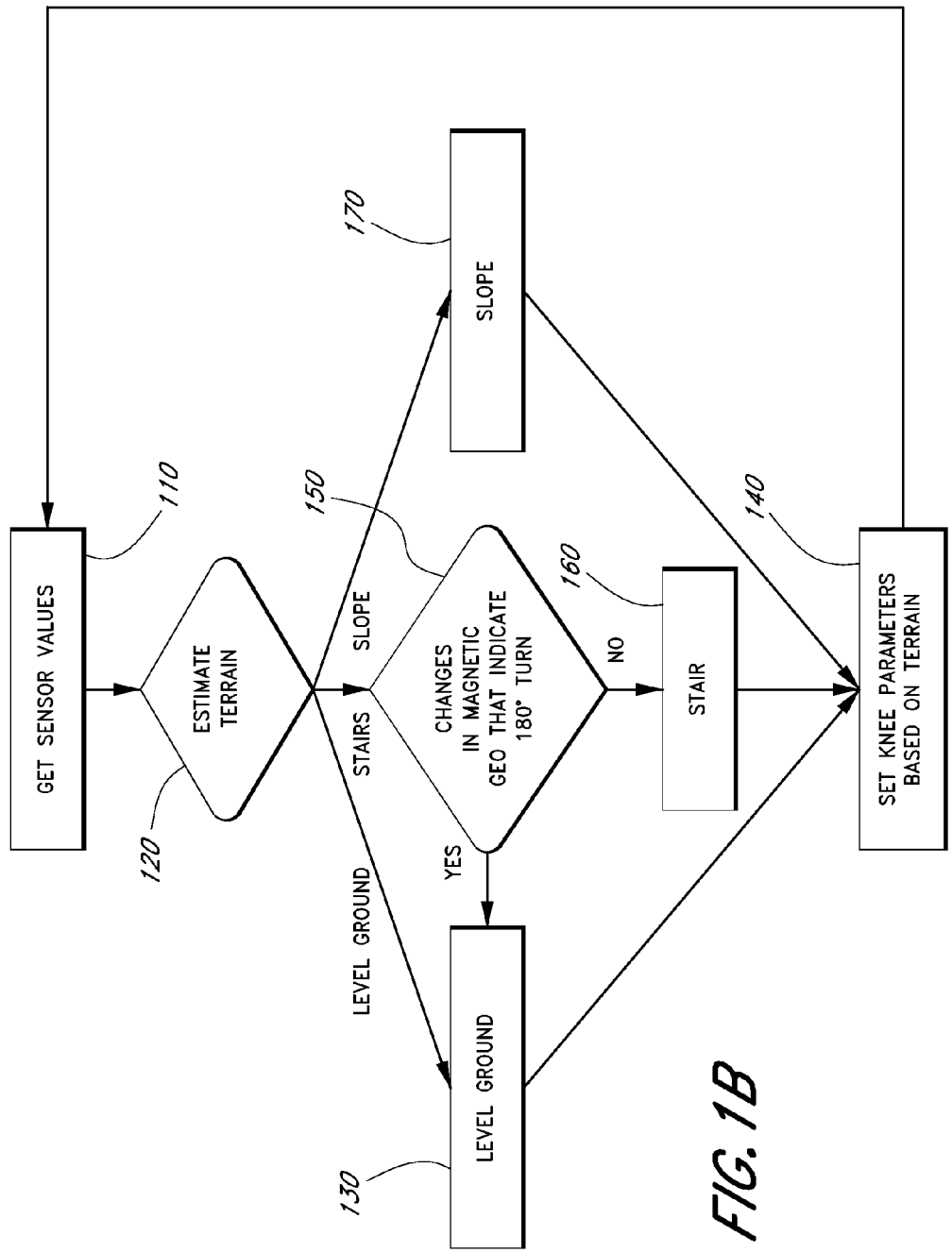
FIG. 1B illustrates a decision tree for a geo-magnetic sensing system on a prosthetic or orthotic device according to one embodiment.

FIG. 1B further illustrates a decision tree for a geo-magnetic sensing system on a prosthetic or orthotic device according to one embodiment. As shown, when the geo-magnetic sensor is integrated with a prosthetic or orthotic device, the sensor can operate to provide feedback information to the device. In certain embodiments, the geo-magnetic sensor obtains sensor values 110, which can include the orientation (i.e., roll, inclination, and azimuth angles) or the position data (x, y, and z). In one embodiment, once the geo-magnetic sensor has collected information related to the sensor values, a processing unit of the prosthetic or orthotic device may estimate the type of terrain 120 the device may encounter.

The processing unit, in certain embodiments, generates an output of "level ground," or "stairs," or "slope" for a prosthetic device such as a prosthetic knee or ankle. In certain embodiments, the geo-magnetic sensor is also capable of determining the degree of slope on which the user is traveling using, for example, the tilt compensation function of certain embodiments of sensors. If the geo-magnetic sensor determines that the device is on level ground 130, the processing unit may then instruct the prosthetic device to set parameters for level ground walking 140. If the geo-magnetic sensor determines that the device is on stairs 160, the processing unit may then instruct the prosthetic device to set parameters for stair case walking 140. However, if the sensor determines that the device is on stairs, but then senses a change indicative of a 180° turn 150, the processing unit may notify the device to resume level ground walking 130 as the device user is likely to be then traveling on a stair case landing. If the geo-magnetic sensor determine that the device is on a slope 170, the processing unit may then instruct the device to set parameters for inclined or declined walking 140. Although FIG. 1B describes a prosthetic knee system, it will be understood from the disclosure herein that other types of prosthetic or orthotic systems (e.g., motion-controlled ankle systems) can also be used.

Figure 2B:
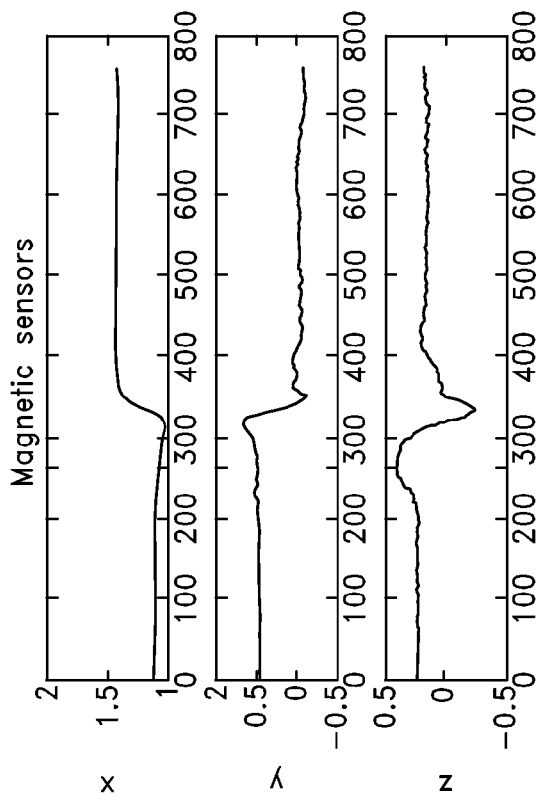
FIGS. 2A and 2B illustrate representative geo-magnetic signal plots of a prosthetic user making a 180 degree rotation when walking and rotating around the same location.
Figure 2A:
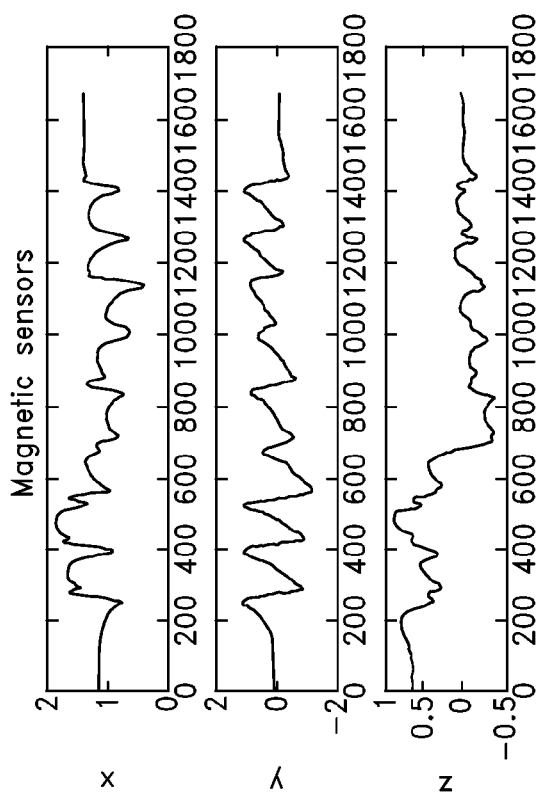

The ability of the geo-magnetic sensor to recognize abrupt changes in direction is demonstrated in FIGS. 2A & 2B. FIGS. 2A & 2B illustrate plots of a geo-magnetic signal charted against the x, y, and z-axes for a prosthetic or orthotic device user as the device user executes certain defined gait patterns. In FIG. 2A, the device user is walking at a steady speed of between about 0.8 meters/second and about 1.2 meters/second. At a position corresponding with sample number 600, the device user executes a 180° turn. In certain embodiments, prosthetic or orthotic devices can have difficulty registering this abrupt change in direction, and the user would experience some instability of movement, which could potentially be dangerous to the already weakened limbs. For example, a typical sensor coupled to a prosthetic or orthotic device, such as an accelerometer or gyroscope, may only be able to measure the speed of movement and not the directionality of movement. Therefore, an abrupt change in direction could potentially throw the device user off-balance. As can be seen at the position corresponding to sample number 600, the geo-magnetic sensor advantageously registers a change in the oscillatory pattern of all three axes and can alert the processing unit that the user has shifted direction.

Similarly, a typical prosthetic or orthotic device can have difficulty with adapting to a prosthetic or orthotic device user who was rotating around the same spot. As described above, the typical prosthetic or orthotic device would simply register that the device was not rapidly changing in acceleration. Therefore, the device user would not be able to compensate for the change in direction and would likely be off-balanced in his or her movements. Other sensors, such as accelerometers and gyroscopes, may have a limited degree of directional sensing, but tend to drift off because of the unexpected sensing pattern or time lag. These sensors are oftentimes, therefore, impractical for rotational movements where the direction continuously changes.

In contrast, geo-magnetic sensors measure direction directly and are therefore more reliable as directional sensing devices. Certain embodiments of the invention using the geo-magnetic sensor can advantageously provide real time information regarding both the orientation and the position data. FIG. 2B illustrates a plot of the device user rotating around the same spot. As can be seen in FIG. 2B, the geo-magnetic sensors demonstrate a shift in all three axes at the location corresponding to around sample number 330. By providing the processing unit with immediate information, the prosthetic or orthotic device is able to adjust to new environments with a much faster processing speed. While FIGS. 2A and 2B illustrate the ability of the geo-magnetic sensor to recognize abrupt changes in direction, such as a 180° turn or rotation around the same spot, certain embodiments can recognize any directional change more than 20°. In yet other embodiments, the sensor can identify directional changes of less than 20°.

Figure 3:
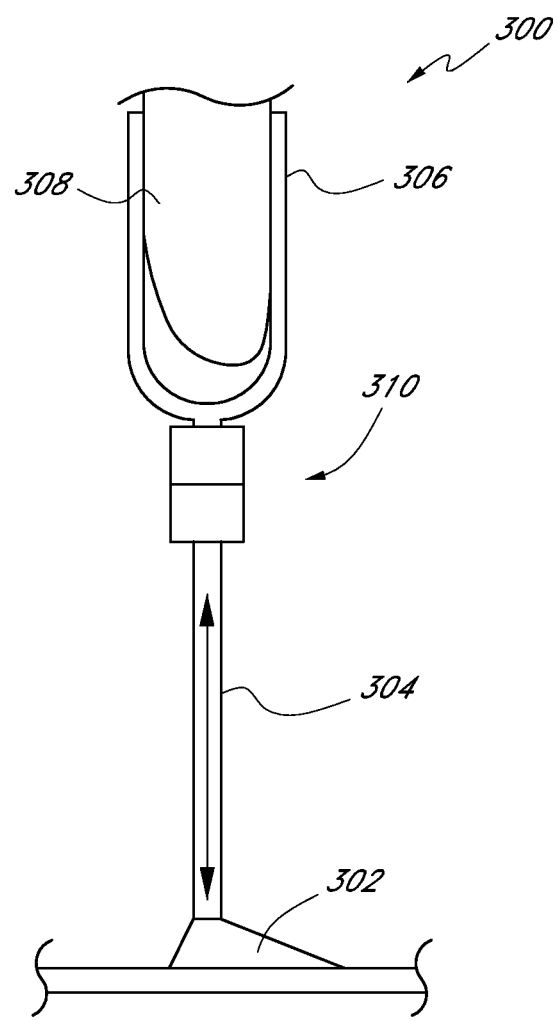
FIG. 3 illustrates a schematic illustration of a lower limb prosthetic assembly according to one embodiment.

In certain embodiments, the geo-magnetic sensor may be adapted for use with a knee device (or ankle device) for a transtibial or transfemoral user. Such devices may include a lower member that is moveable relative to an upper member at a natural human joint location. The upper and the lower members may be articulated about the joint location with respect to each other. Such movement may be actively controlled by an actuator or at least partially dampened, for example, by using a braking mechanism. In certain embodiments, the braking mechanism can include a friction brake, a magnetorheological brake, or a shape memory brake. FIG. 3 is a schematic illustration of an embodiment of a lower limb prosthetic assembly, system or prosthesis 300 including an electronically controlled active knee prosthetic assembly, system or prosthesis 310. In certain embodiments, the knee prosthesis 310 provides resistive forces to substantially simulate the position and motion of a natural knee joint during ambulation and/or other locomotory or stationary activities performed by an amputee. The prosthetic or artificial knee 310 is desirably safe, reliable and generally comfortable to use by the amputee.

The prosthetic lower limb 300 further includes an artificial or prosthetic foot 302 coupled or mechanically connected to a pylon, tube, shaft or shank portion 304 that connects to a distal or bottom portion of the prosthetic knee 310 and a residual limb or stump socket 306 that connects to a top or proximal end of the prosthetic knee 310. The stump socket 306 receives a residual limb or femur portion 308 of the amputee. A suitable pylon or the like can also be provided between the stump socket 306 and the prosthetic knee 310, as needed or desired.

Embodiments of the invention can be practiced with a wide variety of prosthetic feet or ankles. These include Flex-Foot® feet such as Ceterus®, LP Ceterus®, Vari-Flex®, LP Vari-Flex®, Talux®, Elation®, and Proprio Foot®. Some embodiments of suitable prosthetic feet and associated devices are disclosed in U.S. Patent Application Publication No. 2005/0197717, published Sep. 8, 2005, U.S. Patent Application Publication No. 2006/0224246, published Oct. 5, 2006, U.S. Patent Application Publication No. 2006/0224247, published Oct. 5, 2006, the entirety of each of which is hereby incorporated by reference herein.

In certain embodiments, the geo-magnetic sensors may be placed on the top or bottom of a prosthetic foot or ankle plate. In other embodiments, the geo-magnetic sensors may be placed on an ankle joint or the intersection between an ankle plate and a transtibial member. In still other embodiments, the geo-magnetic sensors may be place on an actuator. In still other embodiments, the geo-magnetic sensor may be placed on a transtibial member. A person of skill in the art would understand that these and other embodiments are within the scope of the invention.

Embodiments of the invention can also be practiced with a wider variety of prosthetic knees. These include, but are not limited to the Power Knee™ and the Rheo Knee®. Some embodiments of suitable prosthetic feet are disclosed in U.S. Pat. No. 6,610,101, issued on Aug. 26, 2003, U.S. Pat. No. 6,764,520, issued on Jul. 20, 2004, U.S. Pat. No. 7,314,490, issued on Jan. 1, 2008, U.S. Patent Application Publication No. 2006/0136072, published Jul. 22, 2006, U.S. Patent Application Publication No. 2005/0283257, published Dec. 22, 2005, the entirety of each of which is hereby incorporated by reference herein.

In certain embodiments, the geo-magnetic sensors may be placed on a transtibial member. In other embodiments, the geo-magnetic sensors may be placed on a knee joint or a socket. In still other embodiments, the geo-magnetic sensors may be placed on a transfemoral member. A person of skill in the art would understand that these and other embodiments are within the scope of the invention.

In certain embodiments, the prosthetic knee 310 of embodiments of the invention permits the amputee to move and/or adapt comfortably and safely in a wide variety of circumstances. For example, during walking, running, sitting down, or when encountering subtle or drastic changes in the terrain, topography and environment or ambient conditions, such as, when the user lifts a suitcase or walks down a slope or encounters stairs, among others.

Figure 4:
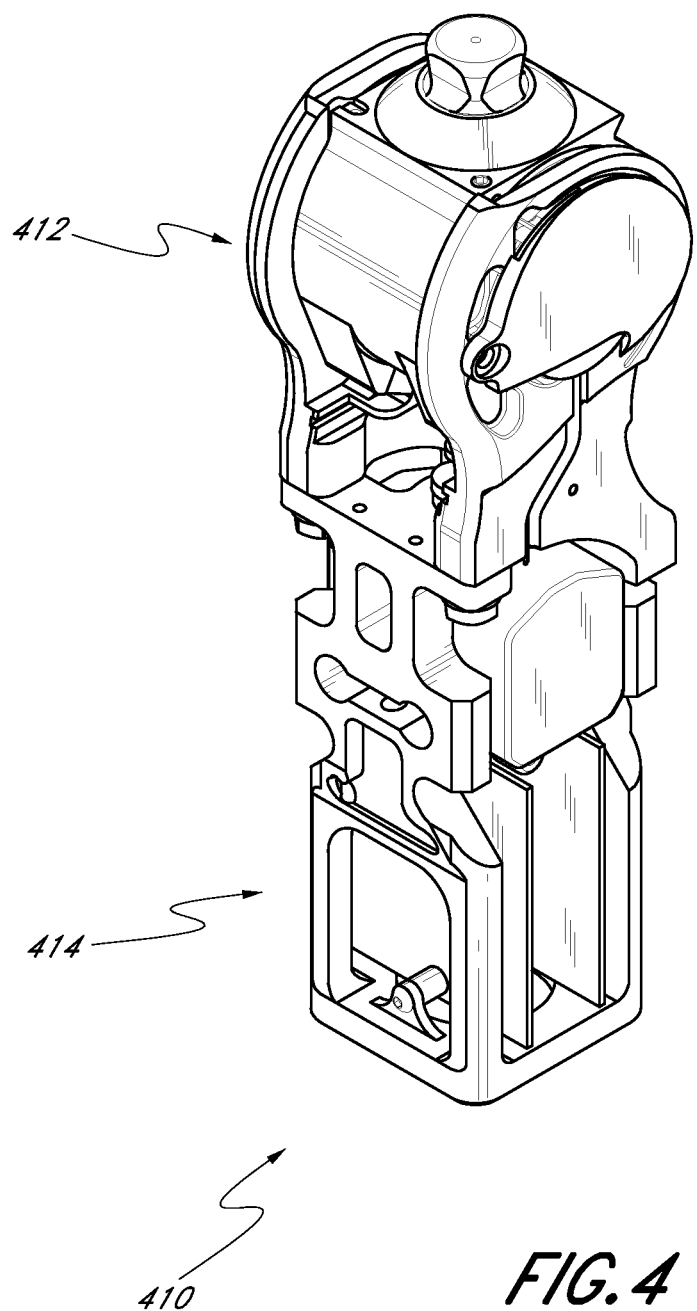
FIG. 4 illustrates a prosthetic knee device suitable for use with a geo-magnetic sensor according to one embodiment.

FIG. 4 shows a prosthetic knee assembly 410 generally comprising the magnetorheological actuator assembly or system 412 and the frame and electronics assembly or system 414. The frame and electronics assembly 414 also provides power and communicates with the actuator assembly 412 via electrical signals.

Figure 5:
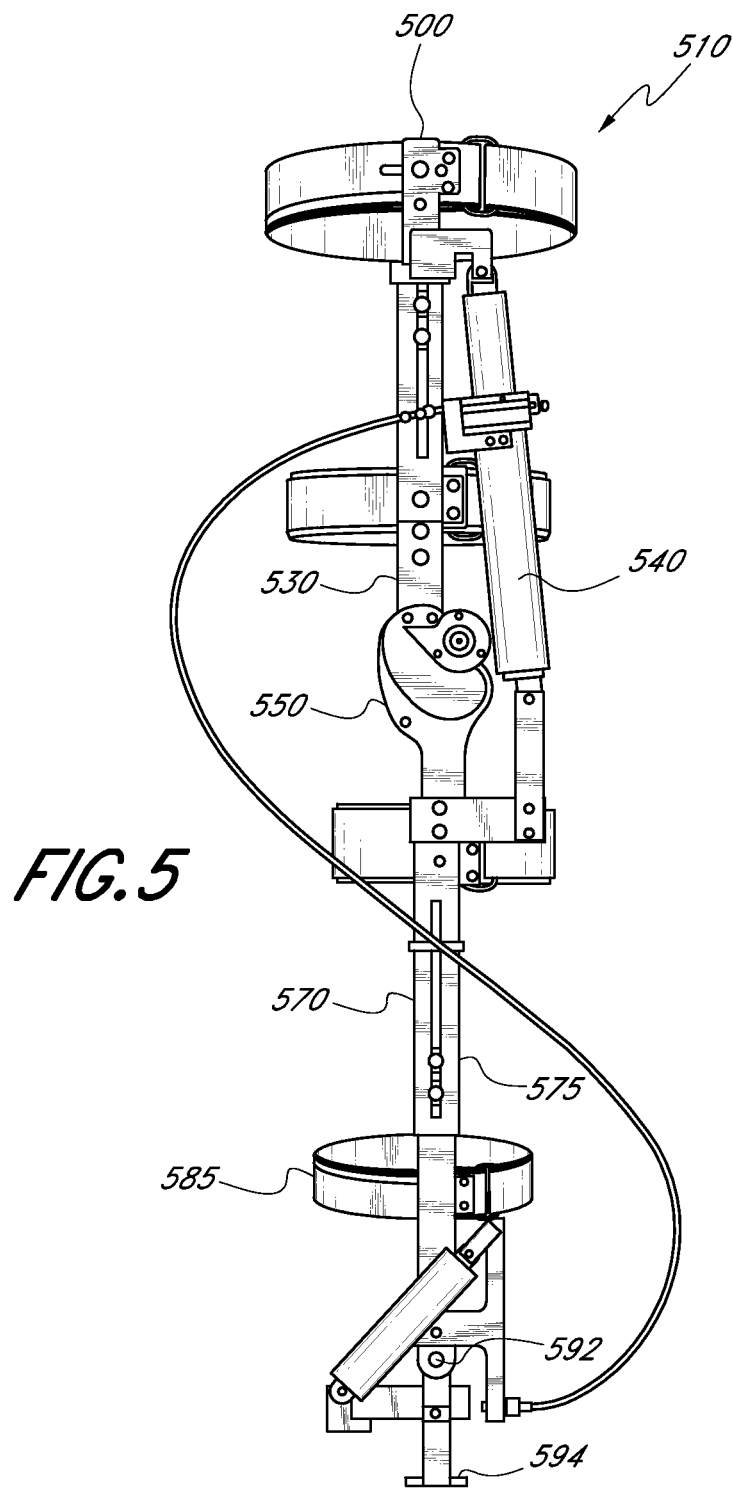
FIG. 5 illustrates an orthotic device suitable for use with a geo-magnetic sensor according to one embodiment.

In certain embodiments, the geo-magnetic sensor may be adapted for use with an orthotic device. As seen in FIG. 5, the orthotic device can be a Knee-Ankle-Foot device, which assists a patient suffering from muscular weakness or other problems affecting the patient's gait by providing support and compensation for diminished muscular function or weakness.

Control of the knee and ankle joints 550, 592 by actuators installed on, and working in conjunction with, the orthotic frame 500 allows the orthotic frame 500 to support a patient's weight during certain activities, while also allowing flexion during other activities. Various ambulatory and related activities performed by a person place different requirements on the function of the orthotic device. The upper and lower frames 530, 570 are preferably adjustable in length, to accommodate fitting to patients of different sizes and physical needs.

Figure 6:
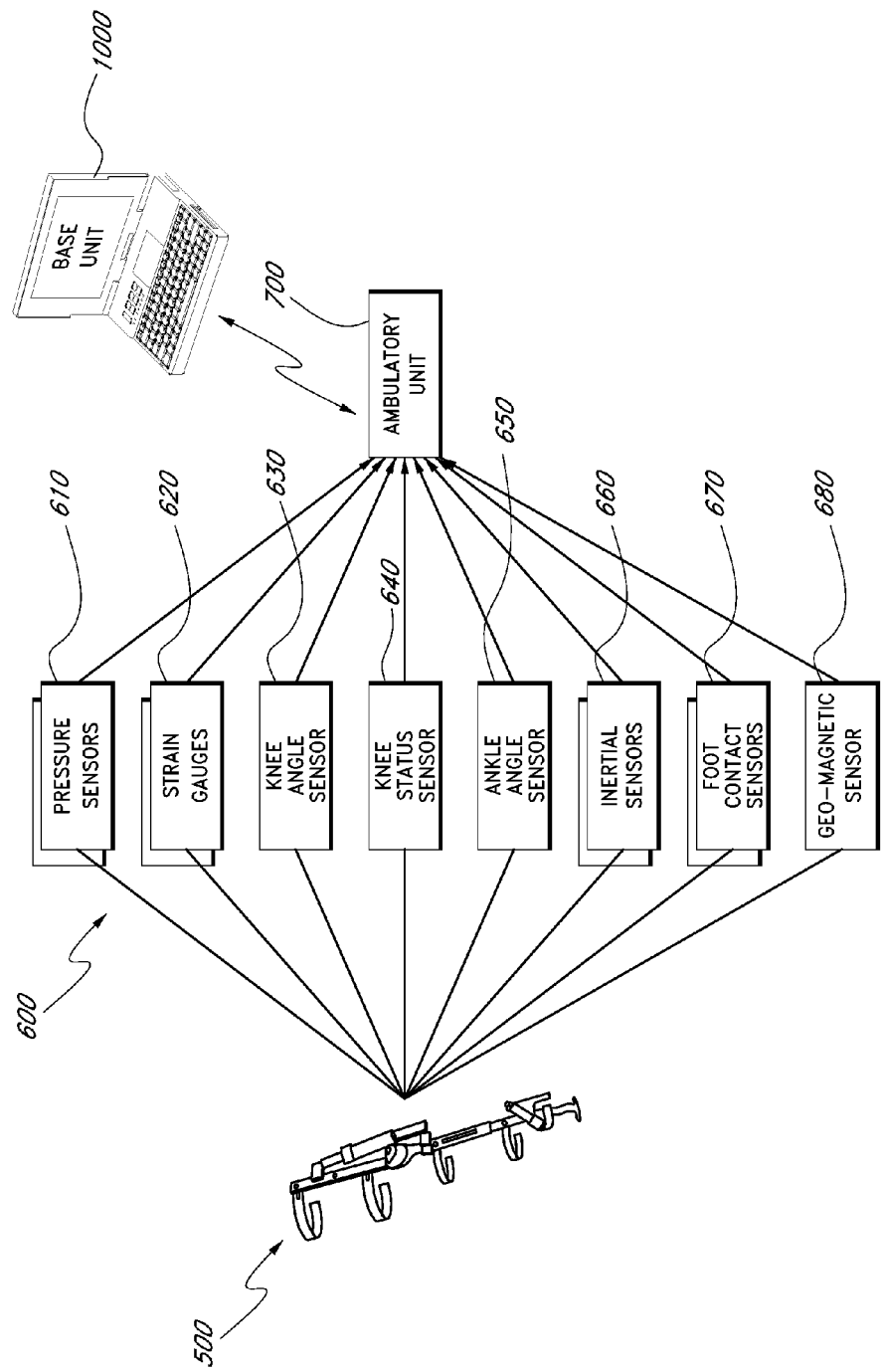
FIG. 6 illustrates a block diagram identifying instrumentation applied to an orthotic device according to one embodiment.

Referring to FIG. 6, the orthotic device is instrumented with a multiple purpose sensor set 600, which enables measurement of physical variables related to comfort (pressure and strain), kinematics (sagittal plane angles of the knee and ankle joints, rotational velocities of the shank and foot segments, and foot accelerations, for example), orientation, knee joint and actuator status, and other events related to ambulatory and related activities, including aspects of the gait cycle such as, for example, initial foot contact, foot flat, heel off, and toe off.

Data gathered from the sensor set 600 may be analyzed for biomechanical evaluation of the patient's use of the orthotic device, which may be useful for fitting of the orthotic device as well as monitoring the patient's progress and diagnosing problems with the patient relating to the orthotic device.

Further, real-time analysis of the data from the sensor set 600 allows identification of ambulatory and related activities that are performed by the patient, and can contribute to functional compensation provided by the orthotic device. For example, in addition to control of the knee device, it can be recognized that a broader range of compensation strategies may be employed based on recognition of different activities such as sitting down, standing up, walking up or down stairs or a slope, or other activities that may place different requirements on the functionality of the orthotic device.

The sensor set may include pressure sensors 610, strain gauges 620, a knee angle sensor 630, a knee status sensor 640, an ankle angle sensor 650, inertial measurement units (IMUs) 660, foot contact sensors 670, and geomagnetic sensors 680. An ambulatory data processing unit (ambulatory unit) 700 can be co-located with the orthosis (mounted to the orthotic frame 500 or carried by the patient, for example), to monitor the sensors and to process sensor data to control actuators of the orthotic device. The ambulatory unit 700 also may provide data communication to a base unit 1000 where further analysis of the sensor data may be performed.

Pressure sensors 610 are disposed on portions of the orthotic frame 500 that interface directly with a patient. In one embodiment, the pressure sensors 610 are strain gages, located on the lateral aspect of each pelotte carrier 585 and protected against mechanical interactions and environmental factors.

Additionally, strain gauges 620 may be disposed on the orthotic frame 500 to measure stresses on the components of the orthotic frame 500 that are related to various ambulatory activities. Strain gauges may be applied to the side bars 575 of the upper and lower frames 530, 570 to measure deformation of the side bars 575 that are related to loading of the side bars 575 during various ambulatory activities, to provide a measurement of the loading.

A knee joint angle sensor 630 may be disposed on or proximate to the knee joint 550, and configured to measure the knee angle (an angle between the proximate and distal frame portions). In one embodiment, the knee joint angle sensor 630 is a precision potentiometer mounted on attaching members of the knee joint 550 to measure the angle in one axis of the knee hinge.

An actuator lock mechanism sensor 640 can be disposed on or proximate to the knee actuator 540 to sense the lock/unlock status of the actuator lock mechanism. In one embodiment, the actuator lock mechanism sensor 640 is a contact switch disposed to determine and lock/unlock status of the actuator lock mechanism based on the position of the actuator lock mechanism.

The actuator lock mechanism sensor 640 can be useful, in addition to simply gathering information for biomechanical evaluation of the orthotic device 510 or the patient, to provide an audible or other signal or warning relating to the lock status of the knee actuator 540. For example, a signal may be generated to indicate to the patient that the knee actuator 540 has been locked, so that the patient can confidently rely on the orthotic device to support her weight. Similarly, an alarm may be generated if a control signal has been sent to lock the knee actuator 540, but the locking mechanism is not properly activated.

Inertial measurement units (IMUs) may be provided on the shank (lower frame 570) and foot parts of the orthotic frame 500. A foot IMU 660 may be positioned below the ankle joint and a shank IMU 660 may be located along the lower (or shank) frame portion 570. The foot IMU 660 may be contained within a housing or small box disposed below the ankle joint, and the shank IMU 660 may be collocated with other electronics or interconnections in a junction or interconnection box located along the shank (distal) frame portion. Each of the IMUs 660 comprises a rate gyroscope and a biaxial accelerometer.

In addition, or alternatively to the IMUs (and other sensors), one or more linear accelerometers may be employed to sense movement or kinematic information of any of the moving parts of the orthotic frame 500. It can be recognized that such linear accelerometers may be employed to provide movement or kinematic information that is unavailable from, or that is redundant to, other sensors.

Foot contact sensors 670 can be provided on the foot plate 594 in the form of pressure sensors or contact switches to detect foot contact with the ground. Foot contact sensors 670 may be located at both front and rear parts of the foot plate 594, to detect both toe (or fore foot) and heel (or rear foot) contact events. The foot contact sensors 670 may be disposed between the foot plate 594 and a soft insole.

Alternative to foot contact sensors 670 provided on the foot plate 594, pressure or contact or other types of sensors may be deployed elsewhere on the orthotic frame 500 to sense foot contact status such as foot strike or lift or related events. For example, accelerometers may detect motion or impact associated with foot strike or lift events, and strain gauges positioned variously about the orthotic frame may provide information relating to the loading of the orthotic frame that may be associated with foot strike and lift events.

One or more geo-magnetic sensors 680 may be disposed on the orthotic frame 500, such as for example a first end near the user's legs, a second end near the user's upper torso, or at any other location in between, and may provide information to the ambulatory unit 700 alone or in combination with the other sensors and gauges. In certain embodiments, the geo-magnetic sensor 680 monitors the directionality of the orthotic device 510 by measuring a first, second, and third data point, corresponding to the orientation (e.g., roll, inclination, and azimuth angles) or the position data (e.g., x, y, z), and sends the data to an ambulatory processing unit 700. The processing unit 700 then compares the first, second, and third data point to a database of predefined gait patterns, such as stored in a memory of the prosthetic device and/or in communication with the prosthetic device.

If the first, second, and third data point recorded over a time interval matches one of the predefined gait patterns designated as "unsafe," the processing unit 700 can send instructions to the orthotic device 510 to issue a warning to alert the device user. Examples of unsafe movements may include sharp sudden turns, higher speed rotations about an axis, and steep declines. In certain embodiments, the time interval over which the data points are recorded is from about 1 millisecond to about 1 second. Thus, monitoring the orientation and providing feedback control benefits the orthotic user by alerting the orthotic user of any sudden shift in direction.

The ambulatory unit 700 can gather kinematic information from the various sensors disposed on the orthotic frame 500. The kinematic information may be processed locally by the ambulatory unit 700, and may be used to control actuators (such as the knee actuator 540) of the orthotic device in response to events or conditions that are detected or recognized by the ambulatory unit 700 based on analysis of the kinematic data. The ambulatory unit 700 also may provide an interface for forwarding gathered data to the base unit 1000 for further processing and analysis.

Figure 7:
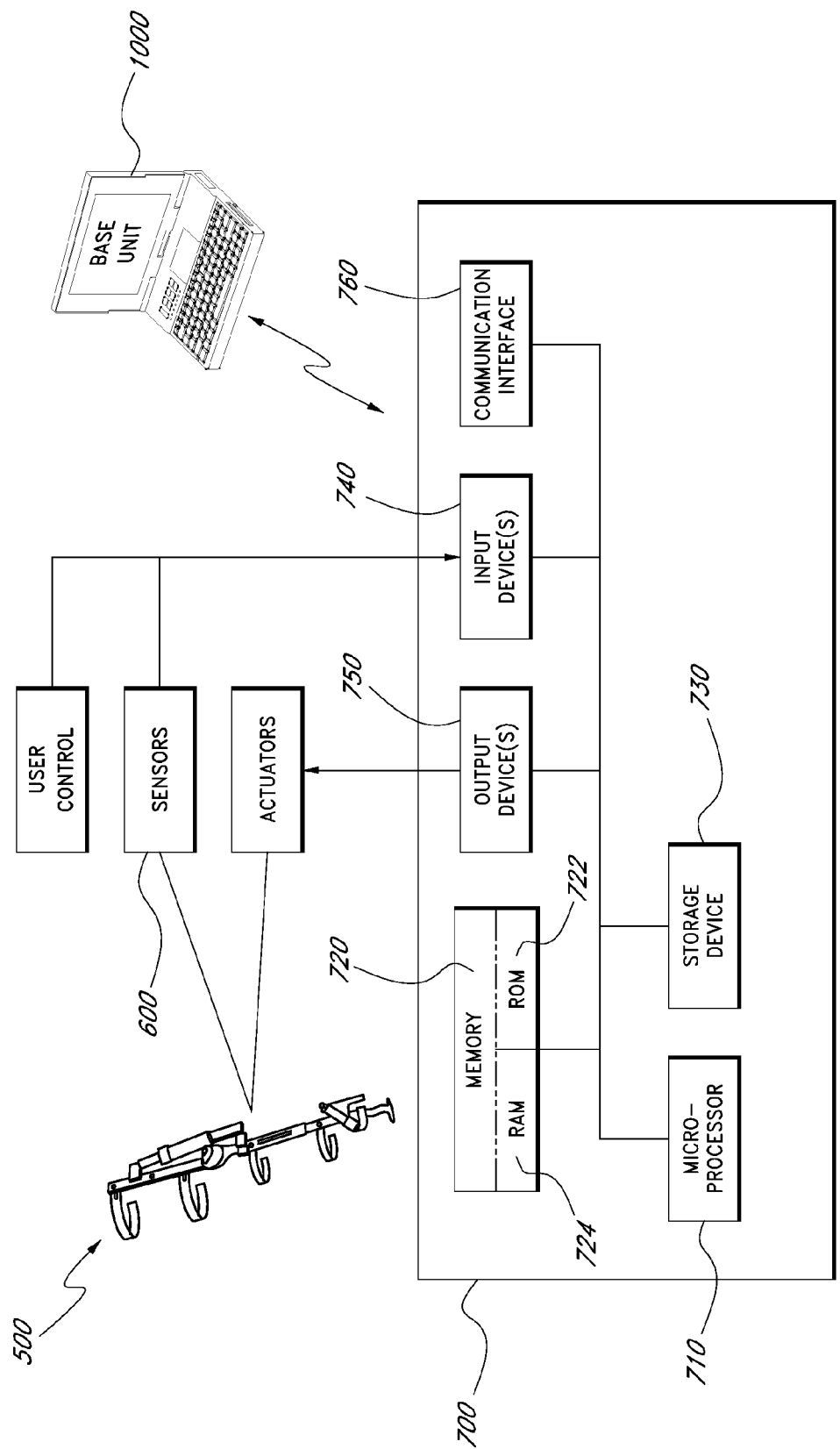
FIG. 7 illustrates a block diagram of an ambulatory control unit for an orthotic device according to one embodiment.

Referring to FIG. 7, the ambulatory unit 700 comprises generally conventional control hardware architecture. Such a control hardware architecture typically comprises a microprocessor 710 connected by a bus (not shown) to an area of main memory 720, comprising both read only memory (ROM) 722, and random access memory (RAM) 724.

The microprocessor 710 may be in communication, via the bus, with a storage device 730 such as a disk storage device or a removable media memory device such as a removable memory card or the like. Input/output devices 740, 750 are included to provide an interface to the sensors and actuators of the orthotic device 510.

A communication interface 760 is provided for communication between the ambulatory unit 700 and the base unit 1000. The communication interface 760 may be a wireless interface, employing an RF, infra-red (IR), or other wireless communication medium. Alternatively, the communication interface 760 may be wired, using a cable in connection with the base unit 1000.

A control program may be stored in the ROM 722, or loaded into memory 720 from storage device 730, for execution by the microprocessor. The control program functions to read sensor data from the sensor inputs, and to evaluate the sensor data for control of actuators of the orthotic frame 500. The control program also may store the sensor data in the storage device 730 for later recall and transmission to the base unit 1000, or transmit the sensor data to the base unit 1000 in real time.

The control program thus reads sensor data for both real-time control of the orthotic device 510 and for later analysis in the base unit 1000. Sensor data sampling rates for real-time functions are typically higher than sampling rates for later analysis. For example, a sampling rate of 100 Hz may be employed for real-time control functions, while a sampling rate of 30 Hz may be employed for data that is merely to be stored for later analysis at the base unit. For data storage, it can be recognized that data rate and the capacity of the storage device 730 influence the amount of information that may be recorded for later analysis.

In the electro-mechanical approach to changing the biasing force of the knee actuator 540, a control program executed by the ambulatory unit 700 can determine when to signal the knee device to select the rigid setting or the flexible setting. While a simple control program may be employed to mimic the mechanical activation of the knee actuator 540, by simply measuring the angle of flexion of the ankle and unlocking the knee actuator 540 at a predetermined angle, a more advanced control program may use a rule-based detection algorithm for the cycle-to-cycle selection of the knee actuator 540 setting based on a more comprehensive sampling of kinetic data of the orthotic frame 500.

Input signals from the sensors may be periodically sampled as inputs to the control program. The control program may consider the knee angle, the ankle angle, the angular velocity of the shank (lower frame 570), the current status of the knee actuator 540 (locked or unlocked), as well as other information.

Figure 8:
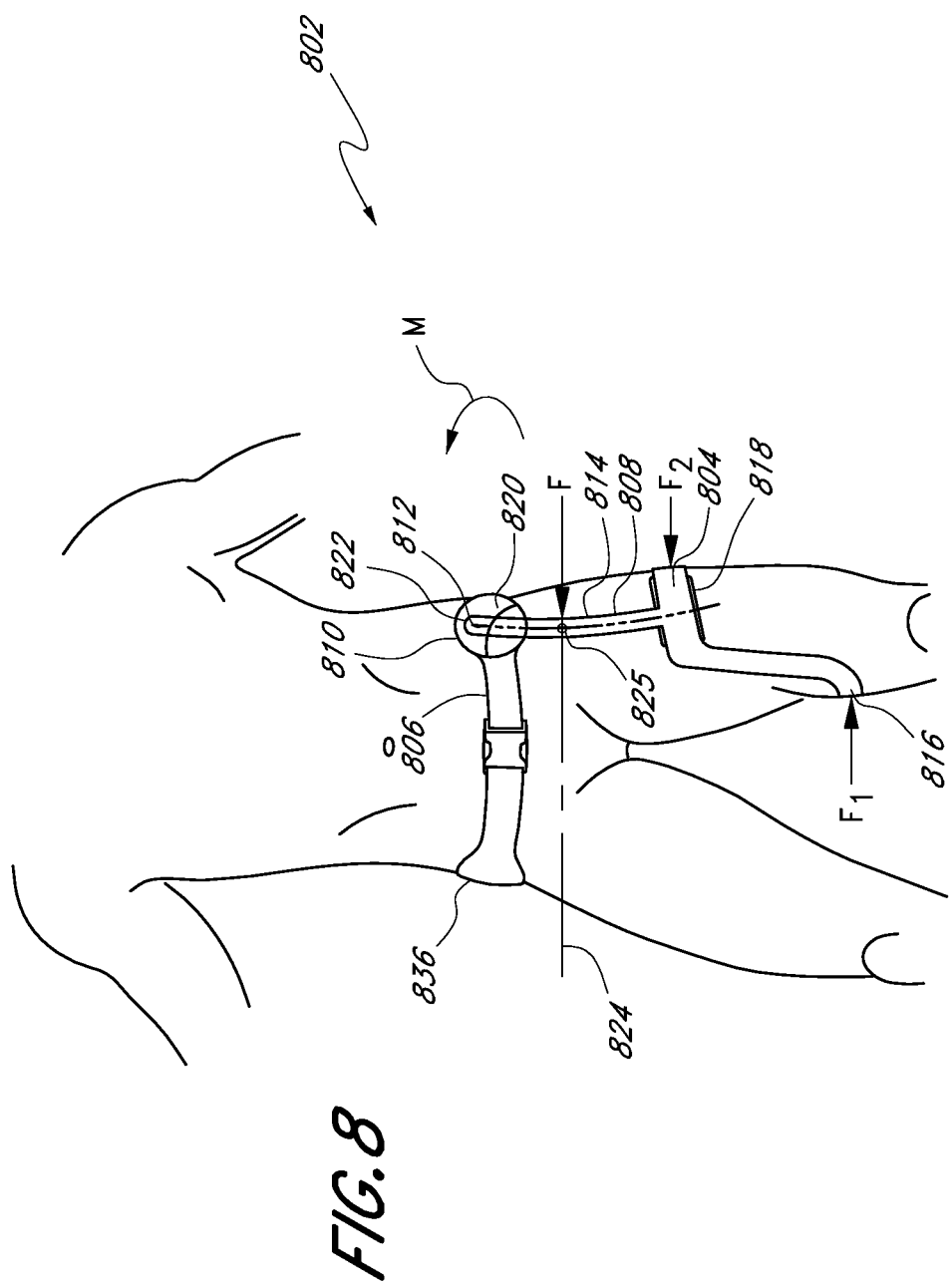
FIG. 8 illustrates another orthotic device suitable for use with a geo-magnetic sensor according to one embodiment.

FIG. 8 shows an embodiment of a hip orthosis 802 for preventing the dislocation of a hip according to one embodiment of the invention. In FIG. 8, the hip orthosis 802 has been fitted to a person in standing position. The orthosis 802 is provided with an upper leg engaging part 804, which is arranged for engaging an upper leg of the person, in use, and a trunk engaging part 806, which is arranged for engaging the trunk of the person, in use.

The trunk engaging part 806 may be provided with a trunk girding part 836 which girds the trunk during use. The upper leg engaging part 804 and the trunk engaging part 806 are intercoupled by means of coupling means 808, 810. The coupling means comprise a connecting part 808 connected with the upper leg engaging part 804 and a coupling part 810 connected with the trunk engaging part 806, which parts 808, 810 are rotatable with respect to each other during use.

In FIG. 8, reference numeral 825 designates a virtual point of rotation, about which point of rotation the trunk engaging part 806 and upper leg engaging part 804 may be rotatable with respect to each other. Here, the orthosis 802, in particular the trunk engaging part 806, is designed such that the virtual point of rotation 825 is, in use, substantially on a virtual line 824 which intersects the two hip balls of the wearer of the orthosis. The connecting part 808 reaches beyond the point of rotation 825, viewed in a direction from the upper leg engaging part 804 towards the point of rotation 825. The coupling part 810 engages the portion of the connecting part 808 reaching beyond the point of rotation 825. The connecting part 808 and the coupling part 810 engage with respect to each other in a point of contact 812.

In FIG. 8, the connecting part 808 may be provided with a resilient element 814. In the embodiment shown, the resilient element 814 comprises a leaf spring from, for instance, metal or plastic. Due to the resilient element 814, the orthosis may be capable of, operatively, exerting a force and/or a moment on the upper leg which makes the upper leg abduct, viewed from the front side of the person, preferably independently of the position of the upper leg with respect to the trunk. In addition, the person has more freedom of movement, since the upper leg can preferably move in all direction. This offers more comfort and the possibility of more efficient exercise of the muscles around the hip joint, which muscles are weakened by, for instance surgery.

In use, the resilient element 814 can exert a force on the upper leg engaging part 804 and the trunk engaging part 806, so that the connecting part 808 and the coupling part 810 are pretensioned with respect to each other. The force is direct such that, in use, the resilient element 814 exerts a force $F_1$ directed outwards on the upper leg via a lower pressure plate 816 of the upper leg engaging part 804, and a force $F_2$ directed inwards on the upper leg via an upper pressure plate 818 of the upper leg engaging part 804. It will be clear that, in this example, the force $F_1$ may be thus directed transversely to the sagittal plane, in the lateral direction, and the force $F_2$ may be thus directed transversely to the sagittal plane, in the medial direction. It will be clear that the resilient element 814 may thus exert moment on the upper leg engaging part 804 and consequently, in use, on the upper leg.

The moment exerted on the upper leg may, for instance, press the hip into its socket. In FIG. 8, the coupling part 810 is provided with a sleeve 820 which prevents an outward movement of an end 822 of the connecting part 808. Here, the end 822 of the connecting part 808 is slidably positioned in the sleeve 820 of the coupling part 810. Consequently, the resilient element 814 exerts a force $F_1$ directed outwards on the coupling part 810 via the end 822 in the point of contact 812. In this example, the force $F_1$ may be thus directed transversely to the sagittal plane, in the lateral direction, for instance along the virtual line 824. The sleeve 820 can be designed as a rigid element from, for instance, metal or plastic, but also as a flexible, elastic, or resilient part from, for instance, rubber or (plastic) cloth.

In FIG. 8, the wearer of the orthosis is in a standing position. The point of contact 812 is then substantially at some distance above the point of rotation 825, and therefore above the line 824. The lower and upper pressure plate 816 and 818, respectively, are substantially below the line 824. As a result, the resilient element 814 may effectively exert a force F and a moment M on the hip joint of the upper leg, which joint is located on line 824, which the force F is directed substantially inwards in the embodiment shown in FIG. 8. In this example, the force F may be thus directed transversely to the sagittal plane, in a medial direction, for instance along the virtual line 824. As a result, the hip is pressed into its socket, so that the risk of dislocation is reduced further. In the embodiment shown in FIG. 8, the moment M is directed such that the knee of the upper leg is pressed substantially outwards, in a direction transverse to the sagittal plane. As a result, too great an adduction of the upper leg (toward the other leg), which increases the risk of dislocation of the hip, can be prevented.

Figure 9:
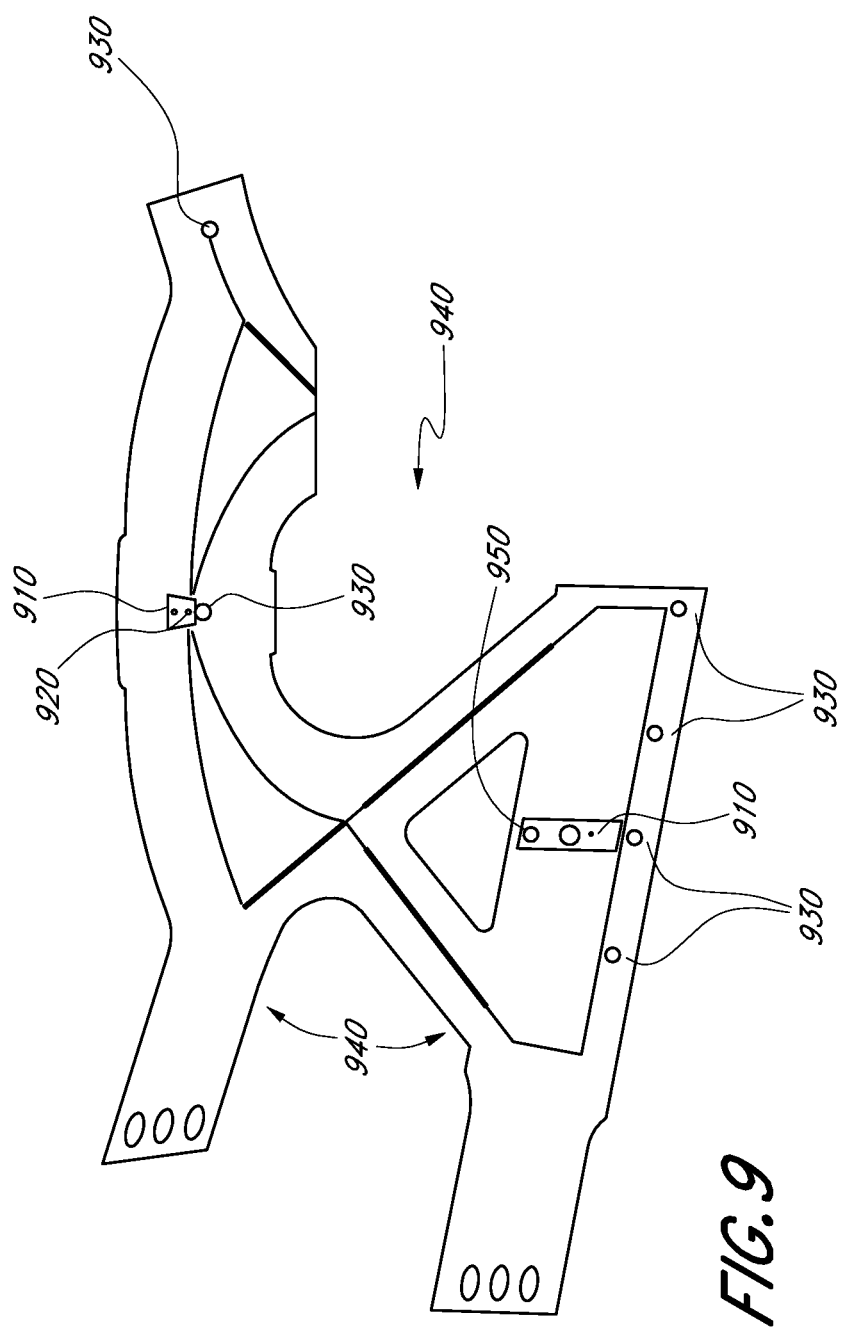
FIG. 9 illustrates another perspective of the orthotic device coupled to a geo-magnetic sensor of FIG. 8.

FIG. 9 illustrates the hip orthosis of FIG. 8 in an open configuration. In certain embodiments, an accelerometer 910 determines the speed of the orthosis user. The geo-magnetic sensor 920 determines the directionality of the orthosis user and initiates a warning in the form of vibration from vibrators 930 when the orthosis user makes a sudden change in direction that may further injure the orthosis user. This sensor 920 coupled with a warning system acts as a physical therapy training tool to help train individuals with weakened limbs how to properly care for their body. The hip orthosis also may include stretch sensors 940 and a battery device 950.

Warning systems may be provided in the prosthetic or orthotic device to alert the user of an unsafe condition that may lead to an injury and/or the impending activation of a feedback or response mechanism. Such a warning system may be utilized to train the user and or the user's muscles in the proper orientations of the joint in order to avoid injuries. Such a warning system may also be utilized to condition an amputee to utilize more efficient biomechanical motions, for example, to achieve proper gait dynamics.

For example, sudden changes in direction may cause instability or even further injury to a device user with a weak hip. If the geo-magnetic sensor senses that the device user is about to execute a U-turn, the processor coupled to the geo-magnetic sensor may trigger the warning system to issue an alarm or vibration to alert the user to stop and use another movement. In certain embodiments, the geo-magnetic sensor facilitates such detection by sending sensory information related to specific gait patterns to the processor, which can then trigger the warning system to alert the prosthetic or orthotic device user if a known unsafe movement is about to be executed. In certain embodiments, the feedback system may dynamically add information to the gait pattern database and the unsafe movement database based on prior gait patterns and movements, which caused increased instability.

As discussed in U.S. Patent Publication Nos. 2009/0024062 and 2009/0024065, both filed on Jul. 18, 2008, each of which is hereby incorporated herein by reference in its entirety, the warning system having feedback characteristics may include, in certain embodiments, sensors, a processor, and one or more feedback notification signals. The warning system may also have a locking mechanism such as an array of air cells insertable into the prosthetic or orthotic device, which inflate when triggered to constrict the limb and prevent unsafe movements. The feedback notification signals may include electric shocks or pulses, flashing lights or LEDs, auditory signals, and tactile signals. The auditory signals may include alarms, buzzers, beepers, whistles, or sirens. The tactile signals may include heat or vibration.

The warning system may include a combination of signals or a combination of signals and a locking mechanism. The warning system may be graduated and begin, for example, by triggering one or more feedback notification signals. If a device user chooses to ignore the signals, the warning system may then trigger the locking mechanism. The warning system may be categorized and trigger different feedback notification signals or the locking mechanism based on the assigned degree of danger of the predicted movement. A signal may last for less than 10 second, less than 5 seconds, or less than 1 second. In other embodiments, the signal will continue until manually turned off. The locking mechanism may last for less than 10 seconds, less than 5 seconds, or less than 1 second. In other embodiments, the locking mechanism may remain locked until manually released.

Moreover, certain control systems and modules described herein may comprise software, firmware, hardware, or any combination(s) of software, firmware, or hardware suitable for the purposes described herein. Software and other modules may be accessible via local memory, via a network, or via other means suitable for the purposes described herein. Data structures or indexes described herein may comprise computer files, variables, programming arrays, programming structures, or any electronic information storage schemes or methods, or any combinations thereof, suitable for the purposes described herein.

Certain embodiments of the invention are also described above with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flowchart and/or block diagram block or blocks.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flowchart and/or block diagram block or blocks. The computer program instructions may also be loaded onto a computer or other programmable data processing apparatus to cause a series of operations to be performed on the computer or other programmable apparatus to produce a computer implemented process such that the instructions which execute on the computer or other programmable apparatus provide means for implementing the acts specified in the flowchart and/or block diagram block or blocks.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A motion-controlled prosthetic or orthotic device comprising:
    a first upper member;
    a second lower member moveable relative to the first upper member at a location generally corresponding to a location of a natural human joint location, wherein the first upper and second lower members are articulated about the joint location with respect to each other;
    at least one geomagnetic sensor disposed on the motion-controlled prosthetic or orthotic device, wherein the at least one geomagnetic sensor is configured to monitor the geomagnetic directionality of the prosthetic or orthotic device with respect to the earth's magnetic field, and to provide associated geomagnetic directionality data; and
    a processor, wherein the processor processes the geomagnetic directionality data to compare the geomagnetic directionality data with predefined unsafe gait patterns related to a change in geomagnetic direction and outputs a command based at least in part on the geomagnetic directionality data matching one of the predefined unsafe gait patterns, wherein the command comprises at least one of an alert command or an instruction to control or restrict movement of the prosthetic or orthotic device,
    wherein when the geomagnetic sensor provides geomagnetic directionality data indicative of a turn greater than 20 degrees while walking, the processor is configured to output a command comprising at least one of an alert command or an instruction to control or restrict movement of the prosthetic or orthotic device to provide a safer response to the turn.

2. The device of claim 1, wherein the sensor is a geomagnetic sensor configured to monitor the geomagnetic directionality of the prosthetic or orthotic device with respect to the earth's magnetic field.

3. The device of claim 2, wherein the geomagnetic sensor comprises a flux gate magnetometer.

4. The device of claim 2, wherein the geomagnetic sensor is further coupled with at least one of an accelerometer or gyroscope.

5. The device of claim 1, wherein the device comprises a prosthetic knee device.

6. The device of claim 1, wherein the turn greater than 20 degrees is about the same spot.

7. The device of claim 1, wherein the command based at least in part on the geomagnetic directionality data matching one of the predefined unsafe gait patterns comprises an instruction to control or restrict movement of the prosthetic or orthotic device.

8. The device of claim 1, wherein the processor further generates an output of at least one of "level ground," "stairs," or "slope."

9. The device of claim 8, wherein when the processor generates an output of "level ground," the processor then instructs the prosthetic or orthotic device to set parameters for level ground walking.

10. The device of claim 8, wherein when the processor generates an output of "stairs," the processor then instructs the prosthetic or orthotic device to set parameters for stair case walking.

11. The device of claim 8, wherein when the processor generates an output of "slope," the processor then instructs the prosthetic or orthotic device to set parameters for inclined or declined walking.

12. A motion-controlled prosthetic or orthotic device comprising:
- a first upper member;
- a second lower member moveable relative to the first upper member at a location generally corresponding to a location of a natural human joint location, wherein the first upper and second lower members are articulated about the joint location with respect to each other;
- at least one sensor disposed on the motion-controlled prosthetic or orthotic device, wherein the at least one sensor is configured to monitor the geomagnetic directionality of the prosthetic or orthotic device, and to provide associated geomagnetic directionality data; and
- a processor, wherein the processor processes the geomagnetic directionality data to compare the geomagnetic directionality data with predefined unsafe gait patterns related to a change in geomagnetic direction and outputs a command based at least in part on the geomagnetic directionality data matching one of the predefined unsafe gait patterns,
- wherein the command comprises at least one of an alert command or an instruction to control or restrict movement of the prosthetic or orthotic device, wherein when the sensor provides geomagnetic directionality data indicative of a 180 degree turn while walking, the processor is configured to output a command comprising at least one of an alert command or an instruction to control or restrict movement of the prosthetic or orthotic device to provide a safer response to the turn.

13. The device of claim 12, wherein the 180 degree turn is about the same spot.

14. The device of claim 12, wherein the command based at least in part on the geomagnetic directionality data matching one of the predefined unsafe gait patterns comprises an instruction to control or restrict movement of the prosthetic or orthotic device.

15. The device of claim 12, wherein the processor further generates an output of "stairs", and when the processor generates an output of "stairs" and the sensor provides geomagnetic directionality data indicative of a 180 degree turn, the processor notifies the prosthetic or orthotic device to resume level ground walking.

* * * * *